US009505836B2

(12) United States Patent
Sand et al.

(10) Patent No.: US 9,505,836 B2
(45) Date of Patent: Nov. 29, 2016

(54) INTERLEUKIN-10 PEPTIDES AND ANTIBODIES THEREOF FOR INHIBITING ADVERSE EFFECTS OF PROTOZOAN INFECTION

(71) Applicant: Wisconsin Alumni Research Foundation, Madison, WI (US)

(72) Inventors: Jordan Marshall Sand, Madison, WI (US); Mark Eric Cook, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 50 days.

(21) Appl. No.: 14/150,354

(22) Filed: Jan. 8, 2014

(65) Prior Publication Data

US 2014/0127220 A1 May 8, 2014

Related U.S. Application Data

(62) Division of application No. 13/548,840, filed on Jul. 13, 2012, now Pat. No. 8,652,457.

(51) Int. Cl.
| | | |
|---|---|---|
| C07K 16/24 | (2006.01) | |
| C07K 16/02 | (2006.01) | |
| C07K 14/54 | (2006.01) | |
| A61K 39/395 | (2006.01) | |
| A61K 39/00 | (2006.01) | |
| A61K 38/00 | (2006.01) | |

(52) U.S. Cl.
CPC ......... *C07K 16/244* (2013.01); *C07K 14/5428* (2013.01); *C07K 16/02* (2013.01); *A61K 38/00* (2013.01); *A61K 2039/505* (2013.01); *C07K 2317/11* (2013.01); *C07K 2317/23* (2013.01); *C07K 2317/34* (2013.01)

(58) Field of Classification Search
None
See application file for complete search history.

(56) References Cited

U.S. PATENT DOCUMENTS

| | | | |
|---|---|---|---|
| 5,741,489 A | 4/1998 | Pimentel | |
| 5,989,867 A * | 11/1999 | Knappe et al. | 435/69.52 |
| 6,608,172 B1 | 8/2003 | Chiou | |
| 8,652,457 B2 | 2/2014 | Sand et al. | |
| 2006/0228448 A1 | 10/2006 | Bolleau et al. | |
| 2009/0022691 A1 | 1/2009 | Moore et al. | |
| 2013/0109619 A1 | 5/2013 | Tarasova et al. | |
| 2014/0127220 A1 | 5/2014 | Sand et al. | |
| 2015/0037277 A1 | 2/2015 | Cook et al. | |

FOREIGN PATENT DOCUMENTS

| | | | |
|---|---|---|---|
| WO | WO/9506657 | * | 3/1995 |
| WO | 2008086621 A1 | | 7/2008 |

OTHER PUBLICATIONS

Hodek et al, Proc. Indian Sci Acad, B69. 2003; No. 4, pp. 461-468.*
Hartog et al, PLoS ONE, 2011, vol. 6, No. 3, pp. 1-10.*
De Meulenaer et al., "Isolation and Purification of Chicken Egg Yolk Immunoglobulins: A Review," Food and Agricultural Immunology, vol. 13(4), 2001.
Collier, et al., "Coccidia-induced mucogenensis promotes the onset of necrotic enteritis by supporting Clostridium perfringens growth," Veterinary Immunology and Immunopathology, vol. 122, 2008, pp. 104-115.
Campbell et al., "Susceptibility to Cryptosporidium parvum Infections in Cytokine- and Chemokine-Receptor Knockout Mice," The Journal of Parasitology, vol. 88(5), Oct. 2002, pp. 1014-1016.
Williams, R.B., "Anticoccidial vaccines for broiler chickens: Pathways to success," available on-line at http://www.tandfonline.com/loi/cavp20 (Jun. 17, 2010).
Alam et al., "A2A adenosine receptor (AR) activation inhibits pro-inflammatory cytokine production by human CD4+ helper T cells and regulates Helicobacter-induced gastritis and bacterial persistence," Nature, vol. 2 (3), May 2009, pp. 232-242.
Cook, M.E., Triennial Growth Symposium: A review of science leading to host-targeted antibody strategies for preventing growth depression due to microbial colonization, J. Animal Sci, vol. 89, 2011, pp. 1981-1990.
Rothwell et al., "Cloing and Characterization of Chicken IL-10 and Its Role in the Immune Response to Eimeria maxima," Journal of Immunology, 2004, vol. 173, pp. 2675-2682.
"Anthelmintic Resistance: An Examination of its Growing Prevalence in the U.S. Cattle Herd", Executive Summary of the 2005 Anthelmintic ResistanceRoundtable; http://www.merck-animal-health-usa.com/binaries/ Anthel_Resist_Exec_Summary_2_tcm96-86774.pdf; 8 pages; 2005.
Arai et al.; "Effects of In Vivo Adminsitration of Anti-IL-10 Monoclonal Antibody on the Host Defence Mechanism Against Murine *Salmonella* Infection"; Immunology;85; pp. 381-388; (1995).
Barnes et al.; "Selection of Different Genotype Larvae and Adult Worms for Anthelmintic Resistance by Persistent and Short-Acting Avermectin/Milbemycins"; International Journal for Parasitology; 31; pp. 720-727; (2001).
Canals, et al.; "Cytokine Profile Induced by a Primary Infection with Ostertagia Ostertagi in Catdtle"; Veterinary Immunology and Immunopathology; 58; pp. 63-75; (1997).
Chen et al; "Oral Administration of a Combination of Select Lactic Acid Bacteria Strains to Reduce the *Salmonella* Invasion and Inflammation of Broiler Chicks"; Poultry Science; 91(9); pp. 2139-2147; (2012).
Coles et al.; "The Detection of Anthelmintic Resistance in Nematodes of Veterinary Importance"; Veterinary Parasitology; 136; pp. 167-185; (2006).

(Continued)

*Primary Examiner* — Bridget E Bunner
*Assistant Examiner* — Fozia Hamud
(74) *Attorney, Agent, or Firm* — Cantor Colburn LLP

(57) ABSTRACT

The present disclosure is directed to interleukin-10 (IL-10) peptides and isolated antibodies that specifically bind to the IL-10 peptides. The IL-10 peptides and the isolated antibodies may be administered alone or as an animal feed additive to treat gastrointestinal protozoan infection in animals.

12 Claims, No Drawings

(56) References Cited

OTHER PUBLICATIONS

Filho et al.; "Humoral and Cellular Immune Response Generated by Different Vaccine Programs Before and After *Salmonella enteritidis* Challenge in Chickens"; Vaccine; 30; pp. 7637-7643; (2012).

Ghebremicael et al.; "Association of Interleukin-10 Cluster Genes and *Salmonella* Response in the Chicken"; Poultry Science; 87(1); pp. 22-26; (2008).

International Search Report and Written Opinion; International Application No. PCT/US2014/047002; International Fling Date Jul. 17, 2014; Date of Mailing Dec. 12, 2014; 14 pages.

Lee et al.; "IL-10 Suppresses Bactericidal Response of Macrophages Against *Salmonella typhimurium*"; Journal of Microbiology; 49(6); pp. 1050-1053; (2011).

Li, Robert W. et al.; "Localized Complement Activation in the Development of Protective Immunity Against Ostertagia Ostertagi Infections in Cattle"; Veterinary Parasitology; 174; pp. 247-256; (2010).

Li, Robert W., et al.; "Local Inflammation as a Possible Mechanism of Resistance to Gastrointestinal Nematodes in Angus Heifers"; Veterinary Parasitology; 145; pp. 100-107p (2007).

Setta et al.; "Early immune dynamics following Infection with *Salmonella enterica* serovars *enteridis, infantis, pullorum* and *gallinarum*: Cytokine and chemokine gene expression profile and cellulsr changes of chicken ceca tonsils"; Comparative Immunology Comparative Immunology, Microbiology and Infectious Diseases, 35 (2012) 397-410.

Symonds et al.; "Bifidobacterium Infantis 35624 Protects Against *Salmonella*-Induced Reductions in Digestive Enzyme Activity in Mice by Attenuation of the Host Inflammatory Response"; Clinical and Translational Gastroenterology; 3, e15; doi:10.1038/ctg.2, 2012.

Co-pending U.S. Appl. No. 13/957,601, filed Aug. 2, 2013; Methods of Reducing *Salmonella* in Poultry.

Wei et al.; "*Salmonella enterica* Serovar Typhi Plasmid Impairs Dendritic Cell Responses to Infection"; Curr Microbiol; 65; pp. 133-140; (2012).

Yazwinski et al.; "Fecal Egg Count Reduction and Control Trial Determinations of Anthelmintic Efficacies for Several Parasiticides Utilizing a Single Set of Naturally Infected Calves"; Veterinary Parasitology; 164; pp. 232-241; (2009).

Sand et al. "Oral Antibody to Interleukin-10 Prevents Growth Suppression by Coccidia Infection"; from Poultry Science Association 101st Annual Meeting Abstracts; Abstract P310; Jul. 9-12, 2012; Poult.Sci. 91(suppl.1) p. 107.

U.S. Appl. No. 13/957,601, filed Aug. 2, 2013; NonFinal Office Action mailed May 7, 2015; 21 pages.

Bork, Peer; "Powers and Pitfalls in Sequence Analysis: The 70% Hurdle"; Genome Research; 10; pp. 398-400; (2000).

Bowie et al.; "Deciphering the Message in Protein Sequences: Tolerance to Amino Acid Substitutions"; Science; 247 (4948); pp. 1306-1310; (1990).

Brown et al.; Tolerance to Single, but Not Multiple, Amino Acid Replacements in Antibody Vh CFR2; J. Immunol.; 156; pp. 3285-3291; (1996).

Burgess, et al.; "Possible Dissociation of the Heparin-binding and Mitogenic Activities of Heparin-binding(Acidic Fibroblast)Growth Factor-1 from Its Receptor-inding Activities by Site-directed Mutagenesis of a Single Lysine Residue"; J.Cell. Biol. 111; pp. 2129-2138; (1990).

Vajdos, et al.; Comprehensive Functional Maps of the Antigen-binding Site of an Anti-ErbB2 Antibody Obtained with Shotgun Scanning Mutagenesis; J. Mol. Biol. 320; pp. 415-428; (2002).

Lazar et al.; "Transforming Growth Factor a: Mutation of Aspartic Acid 47 and Leucine 48 Results in Different Biological Activities"; Molecular and Cellular Biology; pp. 1247-1252; (1988).

Feed Terms and Ingredient Definitions from Association of American Feed Control Officials Inc., 2015 Official Publication, Ali Kashani Section Editor; p. 340; (2015); http://aafco.org/publications/PublicationListing.aspx.

\* cited by examiner

SEQUENCE LISTING

```
<160> NUMBER OF SEQ ID NOS: 20

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Asp Asp Glu Leu Asn Ile Gln Leu
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Asp Gln Met Gly Asp Leu Leu
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic

<400> SEQUENCE: 3

Asp Gln Leu His Ser Leu Leu
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Val Leu Pro Arg Ala Met Gln Thr
1               5
```

```
<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

Val Met Pro Lys Ala Glu Ser Asp
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Val Met Pro Gln Ala Glu Asn His
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

Glu Lys Met Asp Glu Asn Gly Ile
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Ser Lys Leu Gln Glu Arg Gly Val
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic

<400> SEQUENCE: 9

Ser Glu Leu Gln Glu Arg Gly Val
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Glu Pro Thr Cys Leu His Phe Ser
1               5

<210> SEQ ID NO 11
```

```
<211> LENGTH: 8
<212> TYPE: PRT
<213> ORGANISM: Artificial Sequence
<220> FEATURE:
<223> OTHER INFORMATION: Synthetic

<400> SEQUENCE: 11

Glu Asn Ser Cys Ile His Phe Pro
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

Asp Ser Ser Cys Ile His Leu Pro
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic

<400> SEQUENCE: 13

Asp Gln Leu Asn Ser Met Leu
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic

<400> SEQUENCE: 14

Val Met Pro Gln Ala Glu Asn His
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic

<400> SEQUENCE: 15

Asn Met Leu Gln Glu Arg Gly Val
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Asp Ser Ser Cys Thr His Phe Pro
1               5

<210> SEQ ID NO 17
<211> LENGTH: 7
```

```
<212> TYPE: PRT
<213> ORGANISM: Artificial Sequence
<220> FEATURE:
<223> OTHER INFORMATION: Synthetic

<400> SEQUENCE: 17

Asp Asp Leu Glu Ile Gly Leu
1               5

<210> SEQ ID NO 18
<211> LENGTH: 12
<212> TYPE: PRT
<213> ORGANISM: Artificial Sequence
<220> FEATURE:
<223> OTHER INFORMATION: Synthetic

<400> SEQUENCE: 18

Val Leu Pro Thr Ala Ile Ala Asp Met Thr Glu Glu
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Synthetic

<400> SEQUENCE: 19

Thr Gln Met Glu Gly Lys Gly Pro
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic

<400> SEQUENCE: 20

Asn Gln Cys Cys Arg Phe Val
1               5
```

INTERLEUKIN-10 PEPTIDES AND ANTIBODIES THEREOF FOR INHIBITING ADVERSE EFFECTS OF PROTOZOAN INFECTION

CROSS REFERENCE TO RELATED APPLICATION

This application is a divisional of U.S. patent application Ser. No. 13/548,840, filed on Jul. 13, 2012, now U.S. Pat. No. 8,652,457, the disclosure of which is hereby expressly incorporated by reference in its entirety.

INCORPORATION OF SEQUENCE LISTING

A paper copy of the Sequence Listing and a computer readable form of the sequence containing the file name "28243-181 (P120128US02) ST25.txt", which is 3853 bytes in size (as measured in MICROSOFT WINDOWS® EXPLORER) are provided herein and are herein incorporated by reference. This Sequence Listing consists of SEQ ID NOS: 1-20.

BACKGROUND OF THE DISCLOSURE

The present disclosure relates generally to interleukin-10 (IL-10) peptides and to isolated antibodies that specifically bind to the IL-10 peptides. The present disclosure further relates to animal feed additives comprising the IL-10 peptides and/or the isolated antibodies. The present disclosure further relates to methods for treating gastrointestinal protozoan infection, and in particular, maintaining growth in an animal infected with a protozoan infection by administering the IL-10 peptides and the isolated antibodies that specifically bind to the IL-10 peptides.

Coccidiosis is a common parasitic protozoan infection of livestock and poultry species, and is capable of infecting both invertebrates and vertebrates, including humans. Coccidiosis in chickens is caused by infection of the epithelial cells lining the alimentary tract and the cells of associated glands by the parasitic protozoa of the genus *Eimeria*. The *Eimeria* genus includes at least seventeen species capable of infecting birds, most notably *E. tenella, E. necatrix, E. maxima, E. brunette*, and *E. acervulina*.

The life cycle of *Eimeria* takes about four to seven days to complete and begins when active oocysts are ingested by a host. The parasite obtains nutrients from the host and is prolific in nature, although the parasite will generally stop multiplying before causing the death of the host. Coccidiosis disrupts the digestive tract and enteric flora of an animal. Symptoms of the disease include weight loss, growth suppression, diarrhea, bloody diarrhea, anorexia, necrotizing enterocolitis, and sometimes death. Coccidiosis in poultry alone has a severe economical effect. Specifically it is estimated to cost the poultry industry one billion dollars a year in reduced animal performance.

Coccidiosis has generally been treated using anti-Coccidial drugs in animal feed and administering vaccinations using an attenuated Coccidiosis vaccine. Due to the potentially adverse effects on humans and animals, the use of anti-Coccidial drugs and antibiotics is being phased out in many countries including European countries and Japan. In addition, the increased emergence of drug resistant strains and the increased costs of developing new drugs have led to an interest in developing alternative methods for controlling Coccidiosis. Using vaccines for treating Coccidiosis, for example, has many disadvantages, including risk that the vaccine will not generate a sufficient amount of antibodies for treating the infection. Additionally, vaccination requires several weeks to produce antibodies, leaving a several week period in which the immunized birds may become infected with Coccidiosis. Attenuated vaccines may also negatively impact animal growth, resulting in suppression of animal performance.

In light of the current problems associated with controlling Coccidiosis using drugs and/or vaccines, there exists a need for a feed additive capable of treating Coccidiosis and other gastrointestinal protozoan infections, while maintaining growth in an animal. Additionally, there exists a need for a natural feed additive, acceptable by regulatory authorities throughout the world, and which comports with global trends aimed at eliminating drugs and antibiotics from animal feed and the resulting animal products.

SUMMARY OF THE DISCLOSURE

The present disclosure relates generally to IL-10 peptides. More particularly, the present invention relates to IL-10 peptides having an amino acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20. It has been found that these IL-10 peptides, and the isolated antibodies that specifically bind to these peptides, may be used for treating gastrointestinal protozoan infection in animals. Particularly, in one embodiment, the IL-10 peptides and/or the isolated antibodies that specifically bind to the IL-10 peptides may be administered to an animal infected with a gastrointestinal protozoa in an amount effective to maintain the growth of the animal.

In one aspect, the present disclosure is directed to an interleukin-10 peptide including an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

In another aspect, the present disclosure is directed to an isolated antibody that specifically binds to an interleukin-10 peptide including an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

In another aspect, the present disclosure is directed to a method for treating a gastrointestinal protozoan infection in an animal. The method includes administering an interleukin-10 peptide including an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

In another aspect, the present disclosure is directed to a method for treating a gastrointestinal protozoan infection in an animal. The method includes administering to the animal an isolated antibody that specifically binds to an interleukin-10 peptide including an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

In another aspect, the present disclosure is directed to a method of generating an antibody that specifically binds to an interleukin-10 peptide including an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20. The method includes administering the interleukin-10 peptide to an animal.

In another aspect, the present disclosure is directed to an animal feed additive including at least one of an interleukin-10 peptide, an isolated antibody that specifically binds to the interleukin-10 peptide, and combinations thereof. The interleukin-10 peptide includes an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

In another aspect, the present disclosure is directed to an animal feed comprising from about 0.05% by weight to about 1% by weight of an animal feed additive. In one embodiment, the animal feed additive is a dried egg powder. The animal feed additive includes at least one of an interleukin-10 peptide, an isolated antibody that specifically binds to the interleukin-10 peptide, and combinations thereof. The interleukin-10 peptide includes an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, suitable materials and methods are described below.

In accordance with the present disclosure, IL-10 peptides and isolated antibodies that specifically bind to IL-10 peptides, animal feed additives including the IL-10 peptides and the isolated antibodies that specifically bind to IL-10 peptides, and methods for treating gastrointestinal protozoan infection and maintaining growth in an animal infected with a protozoan infection by administering the IL-10 peptides and/or antibodies which specifically bind to IL-10 peptides have been discovered.

Significantly, the IL-10 peptides and isolated antibodies that specifically bind to IL-10 peptides have been found to prevent growth suppression effects typically associated with Coccidiosis infection. Using the IL-10 peptides, isolated antibodies that specifically bind to the IL-10 peptides, and/or animal feed additives containing the IL-10 peptides, antibodies, and combinations thereof avoids significant concerns associated with anti-Coccidial drugs and Coccidial vaccines, including safety concerns, drug resistance concerns, and cost or drug development concerns. Additionally, concerns associated with administering Coccidiosis vaccines, including growth suppression effects and ineffectiveness due to both insufficient antibody production and periods of time between administration of the vaccine and antibody production may be avoided.

Interleukin-10 (IL-10) Peptide and Antibodies Thereof

As noted above, the present disclosure is generally directed to IL-10 peptides and antibodies that specifically bind to the IL-10 peptides for used in animals to treat gastrointestinal protozoan infection. The term "peptide" includes the peptide as well as pharmaceutically acceptable salts of the peptide. "Amino acid residue" means the individual amino acid units incorporated into the peptides of the disclosure. As used herein, the term "amino acid" means a naturally occurring or synthetic amino acid, as well as amino acid analogs, stereoisomers, and amino acid mimetics that function similarly to the naturally occurring amino acids.

As used herein, the term "antibody", or "immunoglobulin", encompasses naturally occurring antibodies, such as polyclonal and monoclonal antibodies, as well as artificial or synthetic antibodies or genetically engineered forms of antibodies, including single chain antibodies, chimeric, and bifunctional antibodies, as well as fragments thereof.

The term "isolated antibody" as used herein, refers to an antibody that is substantially free of other naturally associated molecules, or substantially free of antibodies having different antigenic specificities.

The IL-10 peptide of the present disclosure includes an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20 (see Table 1). In particularly suitable embodiments, the IL-10 peptide has an amino acid sequence selected from the group consisting of SEQ ID NO: 1, SEQ ID NO: 4, SEQ ID NO: 7, and SEQ ID NO: 10.

TABLE 1

Sequence ID NO. and Corresponding Amino Acid Sequence.

| SEQ ID NO: | AMINO ACID SEQUENCE |
|---|---|
| SEQ ID NO: 1 | DDELNIQL |
| SEQ ID NO: 2 | DQMGDLL |
| SEQ ID NO: 3 | DQLHSLL |
| SEQ ID NO: 4 | VLPRAMQT |
| SEQ ID NO: 5 | VMPKAESD |
| SEQ ID NO: 6 | VMPQAENH |

TABLE 1-continued

Sequence ID NO. and Corresponding Amino Acid Sequence.

| SEQ ID NO: | AMINO ACID SEQUENCE |
|---|---|
| SEQ ID NO: 7 | EKMDENGI |
| SEQ ID NO: 8 | SKLQERGV |
| SEQ ID NO: 9 | SELQERGV |
| SEQ ID NO: 10 | EPTCLHFS |
| SEQ ID NO: 11 | ENSCIHFP |
| SEQ ID NO: 12 | DSSCIHLP |
| SEQ ID NO: 13 | DQLNSML |
| SEQ ID NO: 14 | VMPQAENH |
| SEQ ID NO: 15 | NMLQERGV |
| SEQ ID NO: 16 | DSSCTHFP |
| SEQ ID NO: 17 | DDLEIGL |
| SEQ ID NO: 18 | VLPTAIADMTEE |
| SEQ ID NO: 19 | TQMEGKGP |
| SEQ ID NO: 20 | NQCCRFV |

SEQ ID NO: 1, SEQ ID NO: 4, SEQ ID NO: 7, and SEQ ID NO: 10 are amino acid sequences corresponding to four peptides which stimulate IL-10 cytokine production in avian animals, such as chickens, quail, and turkeys. It has been surprisingly found that the IL-10 peptides of the present disclosure prevent growth suppression effects typically associated with gastrointestinal protozoan infection.

The present disclosure is further directed to antibodies that specifically bind to the IL-10 peptides (also referred to herein as "anti-IL-10 antibody"). These antibodies have surprisingly been found to prevent gastrointestinal protozoan growth suppression effects associated with gastrointestinal protozoan infection when isolated and administered thereto. The antibodies of the present disclosure specifically bind to IL-10 peptides including amino acid sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20. In some embodiments, the isolated antibodies specifically bind to IL-10 peptides having an amino acid sequence selected from the group consisting of SEQ ID NO: 1, SEQ ID NO: 4, SEQ ID NO: 7, and SEQ ID NO: 10.

Methods of Generating the Antibodies

The present disclosure is further directed to generating antibodies that specifically bind to the IL-10 peptides. In one embodiment, an antibody is generated by administering the IL-10 peptides described above to an animal. Suitable animals to administer the IL-10 peptides for generating the antibodies may be, for example, avians. Suitable avians may be, for example, chickens, turkeys, ducks, quail, and pheasant. Additional animals include livestock animals such as cows, pigs, sheep, and fish.

Suitable methods for administering the IL-10 peptides to the animal may be, for example by injection or oral administration. Injection and oral admission may include use of an adjuvant such as, for example, Freunds Complete adjuvant and Cholera toxin. Administration may further include conjugation of the IL-10 peptide to a carrier protein such as, for example, bovine gamma globulin.

In one embodiment, antibodies to the IL-10 peptides are generated by an animal (referred to herein as the "producer animal"). When the animal is an avian animal, as know by those skilled in the art, the antibodies generated are passed to the egg, and may specifically be concentrated in the egg yolk of the avian producer animal. Alternatively, antibodies of the present disclosure may be isolated from the animal such as from serum.

The antibodies that specifically bind to IL-10 peptides may be isolated and purified from animal serum or egg using any suitable method known in the art. Such methods include affinity chromatography, as well as other suitable methods for antibody isolation and purification known in the art and described in U.S. Pat. No. 6,608,172 and De Meulenaer et al., "Isolation and Purification of Chicken Egg Yolk Immunoglobulins: A Review," Food and Agricultural Immunology, Vol. 13(4), 2001, hereby incorporated by reference to the extent that they are consistent herewith. In one particularly suitable embodiment, the animal is an avian animal such as a chicken, turkey, duck, or quail, and the antibody can be isolated from the egg yolk of the egg of the avian animal.

In one embodiment, the egg yolk or serum including the antibodies are further dried to form a powder including the antibodies. The whole egg, egg yolk or parts of the egg may be spray dried. Serum may be separated from whole blood according to conventional methods known by those skilled in the art. Spray drying of egg and serum may be performed using conventionally known spray drying methods and commercially available spray drying equipment. Dry egg and serum powders may also be prepared by lyophilization. The dried egg, egg yolk or serum powder may then be introduced into animal feeds as a feed additive to transfer antibodies to an animal.

Animal Feed Additive

The present disclosure is further generally directed to animal feed additives including the IL-10 peptides or isolated antibodies which specifically bind to IL-10 peptides or combinations thereof.

As used herein, the term "feed" broadly refers to any kind of material, liquid or solid that is used for nourishing an animal, and for sustaining normal or accelerated growth of an animal including newborns or young and developing animals. The term includes any compound, preparation, mixture, or composition suitable for intake by an animal. Preferably, the feed is suitable for intake by livestock animals such as cows, pigs, sheep, and fish, as well as avian animals such as quail, ducks, turkeys, and chickens. The term "feed additive" as used herein refers to components typically included in small quantities for the purpose of fortifying basic feed with nutrients, stimulants, medicine, or to promote feed intake or alter metabolism. Feed additives may include pre-mixes of biological compositions, or in the present disclosure, pre-mixes of IL-10 peptide or isolated antibody that specifically binds to IL-10 peptide or combinations thereof.

In one embodiment, the present disclosure is directed to an animal feed additive including IL-10 peptides including an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20. Particularly, the feed additive may include IL-10 peptides having an amino acid sequence selected from the group consisting of SEQ ID NO: 1, SEQ ID NO: 4, SEQ ID NO: 7, and SEQ ID NO: 10, and combinations thereof.

In another embodiment, the present disclosure is directed to an animal feed additive including isolated antibodies that specifically bind to the IL-10 peptide including an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20. In particularly suitable embodiments, the feed additive includes isolated antibodies that specifically bind to IL-10 peptides having an amino acid sequence selected from SEQ ID NO: 1, SEQ ID NO: 4, SEQ ID NO: 7, SEQ ID NO: 10, and combinations thereof.

The IL-10 peptides and/or isolated antibodies which specifically bind to IL-10 peptides may be added to an animal feed as a feed additive or mixed into an animal feed by any method known in the art for mixing feed additives and animal feed. In one embodiment, the IL-10 peptide or isolated antibody which specifically binds to IL-10 peptide may be directly added to the animal feed or mixed with the animal feed just prior to feeding the animal.

The amount of the IL-10 peptide or isolated antibody that specifically binds to IL-10 peptide added and/or mixed with the animal feed depends on the feeding regimen and the type of feed for the animal, and may be determined by those skilled in the art. Typically, the amounts of IL-10 peptides and/or isolated antibodies to IL-10 peptide to be used in an animal feed are summarized in Table 2 below. Antibody prepared using other sources may be calculated as equivalents using Table 2.

TABLE 2

Dose of Anti-IL-10 Antibody in Animal Feed (mg/Kg diet) prepared using egg yolk antibody.

| Source | Low Dose | High Dose |
|---|---|---|
| Affinity purified anti-peptide | 0.0015 | 0.5 |
| Anti-peptide IgY | 0.015 | 50 |
| Dry Immune Yolk | 0.8 | 4000 |
| Dried Immune Whole Egg | 1.5 | 7500 |

Range in doses shown are based on the amount of epitope specific antibody in total IgY (1 to 10%), the amount of IgY in egg (5-10 mg/Kg of feed), antibody losses due to drying storage and gastrointestinal degradation.

The animal feed of the present disclosure may further include optional ingredients including vitamins, minerals, antibiotics, lipids, carbohydrates, proteins, antioxidants, and amino acids.

Suitable vitamins which may be included in the animal feed of the present disclosure include Vitamin A, Vitamin B, Vitamin D, Vitamin E, and Vitamin K.

Suitable minerals which may be included in the animal feed of the present disclosure may include calcium, phosphorus, sodium, potassium, magnesium, chlorine, cobalt, iodine, iron, manganese, copper, molybdenum, zinc and selenium. Common mineral supplements used in poultry feed, for example, include limestone, bone meal, oyster shell, sodium chloride, dicalcium phosphate, manganese sulphate, potassium iodide, and superphosphate.

In some embodiments, one or more antibiotics may be included in the animal feed along with the feed additive. Suitable antibiotics included in the feed may be, for example, penicillin, streptomycin, tetracyclines, and aureomycin.

Suitable lipids included in the animal feed may be, for example, any oil seed, oil and lipid derived from plants or animals. Sources of oilseeds, oils and lipids which may be used in the animal feed include corn, soybean, cotton, lupin, peanut, sunflower, canola, sesame seed oil, olive oil, copra and coconut oil, palm kernels and palm oil, casein, butterfat, lard, fish oils, linseed and oil, tuna oil, tallow and yellow grease, and mixtures thereof.

Suitable carbohydrates which may be included in the animal feed may include starch, cellulose, pentosans, other complex carbohydrates, corn, milo, barley, rye, oats, wheat, wheat middlings, and various grain-by-products.

Suitable sources of protein which may be included in the feed may be, for example, protein obtained from meat meal or fish meal, liquid or powdered egg, fish solubles, whey, milk protein, rice, milo, millet, corn, oats, barley, wheat, rye, wheat bran and/or middlings, soybeans, sesame seeds, peas and beans, sunflower seeds, wheat germ, alfalfa seed, flaxseed, yeast, earthworms, and fish.

Suitable amino acids which may be included in the feed, in addition to the IL-10 peptides disclosed herein, may be, for example, arginine, histidine, isoleucine, leucine, lysine, methionine, phenylalanine, threonine, tryptophan, valine, tyrosine ethyl HCl, alanine, aspartic acid, sodium glutamate, glycine, proline, serine, cystein ethyl HCl, and analogs, and salts thereof.

Suitable antioxidants which may be included in the feed include beta-carotene, Vitamin E, Vitamin C, and tocopherol, or synthetic antioxidants.

Preferably, the animal feed including the feed additive of either IL-10 peptide and/or isolated antibody is a feed for livestock. Preferably, the animal administered the feed composition is selected from the group consisting of cows, pigs, sheep, fish, as well as avian animals such as quail, ducks, turkeys, and chickens.

Methods of Use

The methods of the present disclosure are generally directed to methods for treating gastrointestinal protozoan infection in an animal, and in particular, maintaining growth in an animal infected with a gastrointestinal protozoan infection. In one embodiment, the methods involve injecting or orally administering an IL-10 peptide to an animal, thereby producing antibodies within the animal that specifically bind to the IL-10 peptide. IL-10 cytokine production is associated with down regulation of inflammation, and the IL-10 cytokine functions as an essential immunoregulator of the intestinal tract.

In some embodiments, the methods involve injecting or orally administered an antibody to the IL-10 peptide to an animal. The term "animal", as used herein to describe animals administered an IL-10 peptide or isolated antibody to the IL-10 peptide in accordance with the present disclosure, includes any animal, including a livestock animal, more preferably an animal selected from the group consisting of cows, pigs, sheep, fish, as well as avian animals such as quail, ducks, turkeys, pheasants, and chickens.

It has unexpectedly been found that antibodies that specifically bind to IL-10 peptides treat gastrointestinal protozoan infection in an animal and, additionally, prevent growth suppression typical of gastrointestinal protozoan-infected animals. This is an unexpected surprise, as it is generally known that Coccidiosis infection causes inflammation, which is linked to growth suppression, and that antibody to cytokine IL-10 increases the immune system's inflammatory response, which should thereby lead to increased growth suppression.

Gastrointestinal protozoa include parasites from the kingdom Protozoa. In a suitable embodiment, the protozoa treated by the presently disclosed methods may be from Apicomplexa. Suitable Apicomplexa may be, for example, Coccidiasina. In a particularly suitable embodiment, the protozoa is Eimeriorina such as, for example, Eimeriidae and Cryptosporidiidae. In a particularly suitable embodiment, the protozoa is selected from the group consisting of *Cryptosporidium, Eimeria acervulina, Eimeria tenella, Eimeria maxima* and *Eimeria brunetti*.

In one aspect, the present disclosure is directed to methods for preventing gastrointestinal protozoan infection and maintaining growth in an animal infected with protozoan infection or at risk of protozoan infection by administering isolated antibodies that specifically bind to IL-10 peptides including amino acid sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20. For example, the methods may include administering isolated antibodies that specifically bind to IL-10 peptides having an amino acid sequence selected from the group consisting of SEQ ID NO: 1, SEQ ID NO: 4, SEQ ID NO: 7, SEQ ID NO: 10, and combinations thereof. As used herein "at risk of" refers to having little resistance to a certain condition or disease (i.e., protozoan infection), including being genetically predisposed, having a family history of, and/or having symptoms of the condition or disease, and being exposed to other animals that have been exposed to or have the condition or disease.

Additionally, the IL-10 peptides and/or isolated antibodies may further be used as a feed additive for animal feed. The animal feed may be administered to an animal to treat protozoan infection in the gastrointestinal tract of an animal.

The disclosure will be more fully understood upon consideration of the following non-limiting Examples.

EXAMPLES

Example 1

Detection of Antibody Production

In this Example, the concentration of anti-IL-10 antibody production contained within the egg yolk of IL-10 peptide-administered producer hens was determined by using Enzyme-linked immunosorbent assay (ELISA) techniques.

Specifically, each of four IL-10 peptides selected from the group consisting of IL-10 Peptide #1 (SEQ ID NO: 1), IL-10 Peptide #2 (SEQ ID NO: 4), IL-10 Peptide #3 (SEQ ID NO: 7), and IL-10 Peptide #4 (SEQ ID NO: 10) was conjugated to hen ovalbumin (OVA, Sigma, St. Louis, Mo.) for ELISA using glutaraldehyde procedure. A 96-well Nunc immunosorbent F-series microplate (Sigma, St. Louis, Mo.) was coated with 100 µg/plate of peptide-specific OVA conjugate in sodium carbonate coating buffer having a pH of 9.6. The plate was allowed to coat overnight (100 µl well) at 4° C. Dry egg yolk samples containing antibody to IL-10 Peptide #1, #2, #3, or #4 were diluted 1:10 in acidic PBS having a pH of 4 and allowed to incubate overnight at 4° C. After overnight incubation, the plate was washed 6 times with PBS/0.5% Tween solution, blocked with non-protein blocking buffer (175 µl well, Pierce Scientific, Rockford, Ill.), and allowed to incubate at room temperature for at least 1 hour. The plate was washed 6 times and then samples of either FCA control or antibody were added at a concentration of 100 µl well in duplicate at 10× serial dilutions starting at 1:1000. Primary antibodies were incubated for 1 hour, the plate was washed 6 times, and then secondary antibody (HRP-conjugated goat anti-chicken antibody, Bethyl Labs, Montgomery, Tex.) was diluted in blocking buffer 1:5000 and added at a concentration of 100 µl well. Secondary antibody was incubated for 30 minutes, and then substrate solution containing 19.74 ml 0.05M sodium acetate, 100 µl 20 mg/mL 3,3',5,5' Tetramethyl Benzidine (TMB), 128 µl 0.5M H2O2 was added at a concentration of 125 µl well and allowed to incubate until sufficient color development during the linear phase of development (blue color indicates primary antibody presence). A stop solution (0.5M sulfuric acid) was added to produce a yellow stable color and the plate was read at 450 nm on a Biotek EL800 plate reader. Duplicate optical densities were averaged and blocking buffer background was subtracted to produce a final optical density. Optical density of antibody to IL-10 peptides #1-4 and FCA control were compared to determine specificity and dose level used in the final chick experiment (see Table 3).

TABLE 3

Optical Densities of Anti-IL-10 Peptides.

| Dilution | IL-10 #1 | IL-10 #2 | IL-10 #3 | IL-10 #4 |
|---|---|---|---|---|
| 10 | 1.0585 | 0.935 | 0.968 | 0.8822 |
| 100 | 1.049 | 1.006 | 0.973 | 0.9 |
| 1000 | 0.9705 | 1.033 | 1.001 | 0.678 |
| 10000 | 0.4795 | 0.6775 | 0.593 | 0.224 |
| 100000 | 0.075 | 0.129 | 0.115 | 0.059 |
| 1000000 | 0.028 | 0.03 | 0.037 | 0.03 |
| 10000000 | 0.059 | 0.016 | 0.027 | 0.028 |
| 100000000 | 0.022 | 0.0055 | 0.0181 | 0.033 |
| FCA | 0.562 | | 0.499 | 0.60 |

Example 2

Chicks Fed Antibody to IL-10 Peptide

In this Example, the use of isolated anti-IL-10 antibody to prevent growth suppression due to Coccidiosis infection was determined.

Specifically, Single Comb White Leghorn laying hens were injected with one of four IL-10 peptides: IL-10 peptide #1 (SEQ ID NO: 1), IL-10 peptide #2 (SEQ ID NO: 4), IL-10 peptide #3 (SEQ ID NO: 7), or IL-10 peptide #4 (SEQ ID NO: 10). Egg antibodies directed against the four hydrophilic, antigenic and accessible peptides of IL-10 were then produced in the laying hens. More specifically, the egg antibodies were directed against IL-10 peptide #1 (SEQ ID NO: 1), IL-10 peptide #2 (SEQ ID NO: 4), IL-10 peptide #3 (SEQ ID NO: 7), or IL-10 peptide #4 (SEQ ID NO: 10). Egg yolks were collected from the producer hens, lyophilized, and the egg powder was added to feed at a concentration of 3.41 grams of egg powder/Kg feed. Heavy breed broiler chicks were then divided into five groups of at least 40 chicks/group. Four of the groups were fed egg antibody specific to IL-10 Peptides #1-4. The fifth group, or the control group, was fed egg antibody or egg antibody collected from hen injected with Freund's complete adjuvant and no IL-10 peptides. Three days following egg antibody feeding, half of all five groups of chicks were either subjected to oral gavage with saline and half were subjected to a 10× dose of live attenuated Coccidiosis mixture, the mixture consisting of the following *Eimeria* species: *Eimeria acervulina, Eimeria tenella, Eimeria maxima,* and *Eimeria brunetti* (ADVENT® Coccidiosis Vaccine control, Novus Intl., St. Charles, Mo.). The chicks were then monitored for 7 days, or from day 3 to day 10, for weight gain post-Coccidiosis infection.

As shown in Table 4, demonstrating the composite results of the study carried out twice, the Coccidiosis-exposed chicks in each of the four groups fed antibody to IL-10 Peptides #1-4 demonstrated greater weight gain (in grams) than the control fed Coccidiosis-exposed chicks. Of the four groups of Coccidiosis-exposed chicks fed antibody to IL-10 peptides, chicks fed antibody to IL-10 Peptide #2 demonstrated the greatest weight gain as compared to the other three groups of chicks fed antibody to IL-10 peptides #1, #3, and #4. Additionally, weight gain for chicks fed antibody to IL-10 Peptide #2 approached that found in non-Coccidiosis exposed control chicks. Chicks not exposed to Coccidiosis and fed antibody to IL-10 peptides in all four groups showed greater weight gain than the control fed chicks not exposed to Coccidiosis.

TABLE 4

Effect of Feeding Anti-IL-10 on Growth Response after 7 Days (in grams)

| Antibody | No Coccidiosis | Coccidiosis |
|---|---|---|
| Control | 192 | 174 |
| Anti-IL-10 #1 | 193 | 177 |
| Anti-IL-10 #2 | 195 | 185 |
| Anti-IL-10 #3 | 200 | 180 |
| Anti-IL-10 #4 | 196 | 175 |

Table 5 demonstrates the average rate of weight gain (in grams) in a two day period for Coccidiosis-exposed chicks fed control antibody versus antibody to IL-10 peptide #2. Table 3 also demonstrates the average total rate of weight gain (in grams) in a 7-day period for Coccidiosis-exposed chicks fed control antibody versus antibody to IL-10 peptide #2. As shown in Table 3, Coccidiosis-exposed chicks fed antibody to IL-10 peptide #2 demonstrated a greater weight gain (in grams) as compared to Coccidiosis-exposed control-fed chicks.

TABLE 5

Effect of Feeding Anti-IL-10 on Growth Response after 2 Days and after 7 Days (in grams)

| Antibody | Average Rate of Weight Gain in 2 Day Period | Average Rate of Weight Gain in 7 Day Period |
|---|---|---|
| FCA Control | 43.1 | 173.7778 |
| Anti-IL-10 #2 | 48.4 | 195.1333 |

These results suggest that the chicks infected with Coccidiosis and fed control antibody had suppressed growth rates as compared to chicks not infected with Coccidiosis and fed control antibody. Thus, these results suggest that Coccidiosis infection contributes to growth suppression in chicks infected with Coccidiosis. Further, these results suggest that isolated antibodies to IL-10 peptides #1-4 prevent growth suppression caused by Coccidiosis infection. These results also suggest that feeding isolated anti-IL-10 peptides to healthy broiler chicks does not adversely affect growth, but may actually improve growth in healthy chicks.

Example 3

Hens Injected with IL-10 Peptides and Passive Transfer of Antibody to IL-10 Peptides to Hatched Chicks In this Example, the use of antibodies, specific to IL-10 peptides, which were passively transferred to hatched chicks to prevent growth suppression due to Coccidiosis, was determined.

Single Comb White Leghorn laying hens were divided into five groups. Four groups were injected with four IL-10 peptides: IL-10 peptide #1 (SEQ ID NO: 1), IL-10 peptide #2 (SEQ ID NO: 4), IL-10 peptide #3 (SEQ ID NO: 7), and IL-10 peptide #4 (SEQ ID NO: 10). The fifth group, or control group, was injected with Freund's complete adjuvant alone. Twenty-one days after the first injections, hens were inseminated, fertile eggs incubated, and chicks were hatched with the circulating antibodies. Three days after the chicks hatched, the chicks were injected with a 10-dose of live attenuated Coccidiosis mixture, the mixture consisting of the following *Eimeria* species: *Eimeria acervulina, Eimeria tenella, Eimeria maxima,* and *Eimeria brunetti* (ADVENT® Coccidiosis Vaccine control, Novus Intl., St. Charles, Mo.). Growth was determined for 7 days, or from day 3 to day 10, following injection with the Coccidiosis vaccine.

As shown in Table 6, the Coccidiosis-exposed chicks with circulating antibody to IL-10 peptides showed greater weight gain as compared to Coccidiosis-exposed chicks with circulating control antibody. Coccidiosis-exposed chicks without circulating antibody to IL-10 peptides showed less weight gain as compared to non-Coccidiosis exposed chicks without circulating antibody to IL-10 peptides.

TABLE 6

Effect of Coccidiosis and Circulating Anti-IL-10 on Growth (in grams)

| Antibody | Control | Anti-IL-10 |
|---|---|---|
| No Coccidiosis | 95(2) | 97(2) |
| Coccidiosis | 87(4) | 96(3) |

Table 7 shows the average weight gain (in grams) for Coccidiosis-exposed chicks with circulating antibody to IL-10 Peptide #4 as well as non-Coccidiosis exposed chicks with circulating antibody to IL-10 Peptide #4. Table 5 also shows the average weight gain (in grams) for Coccidiosis-exposed chicks with circulating control antibody as well as non-Coccidiosis exposed chicks with circulating control antibody. Table 5 demonstrates that Coccidiosis-exposed chicks with circulating antibody to IL-10 peptide #4 had a greater weight gain as compared to the chicks with circulating control antibody, both exposed and not exposed to Coccidiosis. Table 5 further demonstrates that the Coccidiosis-exposed chicks with circulating control antibody gained less weight than non-Coccidiosis exposed chicks with circulating control antibody. Table 5 further demonstrates that non-Coccidiosis exposed chicks with circulating antibody to IL-10 peptide #4 had a greater weight gain than non-Coccidiosis-exposed chicks with the circulating control antibody.

TABLE 7

Effect of Circulating Anti-IL-10 #4 on Growth
Response Following Coccidiosis Exposure (in grams)

| Antibody | Coccidiosis | No Coccidiosis |
|---|---|---|
| FCA Control | 87.083 | 94.583 |
| Anti-IL-10 #4 | 96.071 | 97.266 |

These results suggest that Coccidiosis infection contributes to growth suppression in chicks infected with Coccidiosis. These results also suggest that administering IL-10 peptides to hens causes the hens to passively transfer the antibodies that specifically bind to IL-10 peptides to their chicks. Furthermore, these results suggest the passively transferred antibodies that specifically bind to IL-10 peptides prevent growth suppression caused by Coccidiosis infection. Lastly, these results suggest that administering IL-10 peptides to animals does not adversely affect growth, but may actually improve growth in healthy chicks.

In view of the above, it will be seen that the several advantages of the disclosure are achieved and other advantageous results attained. As various changes could be made in the above peptides and methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. An animal feed comprising from about 0.15 mg/kg to about 50 mg/kg of an animal feed additive comprising an isolated antibody that specifically binds to an interleukin-10 peptide, the interleukin-10 peptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

2. The animal feed of claim 1, wherein the interleukin-10 peptide comprises an amino acid sequence selected from the group consisting of SEQ ID NO: 1, SEQ ID NO: 4, SEQ ID NO: 7, and SEQ ID NO: 10.

3. The animal feed of claim 1, wherein the isolated antibody is an avian egg antibody.

4. The animal feed of claim 3, wherein the avian egg antibody is concentrated in the egg yolk.

5. The animal feed of claim 4, wherein the egg yolk is dried.

6. The animal feed of claim 1, wherein the antibody is a monoclonal antibody, a synthetic antibody, or a genetically engineered antibody.

7. An animal feed additive comprising egg yolk, the egg yolk comprising anti-interleukin-10 antibodies, wherein the anti-interleukin-10 antibodies specifically bind to an interleukin-10 peptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

8. The animal feed additive of claim 7, wherein the anti-interleukin-10 antibodies in the egg yolk comprise total 1 to 10% by weight of the total IgY in the egg yolk.

9. The animal feed additive of claim 7, wherein the interleukin-10 peptide comprises an amino acid sequence selected from the group consisting of SEQ ID NO: 1, SEQ ID NO: 4, SEQ ID NO: 7, and SEQ ID NO: 10.

10. An animal feed comprising animal feed additive comprising egg yolk, the egg yolk comprising anti-IL-10 antibodies, wherein the anti-IL-10 antibodies specifically bind to an interleukin-10 peptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

11. The animal feed of claim 10, wherein the anti-interleukin-10 antibodies in the egg yolk comprise total 1 to 10% by weight of the total IgY in the egg yolk.

12. The animal feed of claim 10, wherein the interleukin-10 peptide comprises an amino acid sequence selected from the group consisting of SEQ ID NO: 1, SEQ ID NO: 4, SEQ ID NO: 7, and SEQ ID NO: 10.

* * * * *